(12) United States Patent
Lucas et al.

(10) Patent No.: US 10,049,553 B2
(45) Date of Patent: Aug. 14, 2018

(54) DEVICE FOR MONITORING THE OPERATION OF A DOSAGE DISPENSER OF A LIQUID ADDITIVE IN A MAIN LIQUID, AND DOSAGE DISPENSER PROVIDED WITH SUCH A DEVICE

(71) Applicant: DOSATRON INTERNATIONAL, Tresses (FR)

(72) Inventors: Gregory Lucas, Saint-Loubes (FR); Alexandre Hardoin, Bordeaux (FR)

(73) Assignee: DOSATRON INTERNATIONAL, Tresses (FR)

( * ) Notice: Subject to any disclaimer, the term of this patent is extended or adjusted under 35 U.S.C. 154(b) by 0 days.

(21) Appl. No.: 15/308,956

(22) PCT Filed: May 4, 2015

(86) PCT No.: PCT/IB2015/053242
§ 371 (c)(1),
(2) Date: Nov. 4, 2016

(87) PCT Pub. No.: WO2015/170238
PCT Pub. Date: Nov. 12, 2015

(65) Prior Publication Data
US 2017/0084157 A1 Mar. 23, 2017

(30) Foreign Application Priority Data
May 6, 2014 (FR) .................................... 14 54074

(51) Int. Cl.
| | | |
|---|---|---|
| *G08B 21/18* | (2006.01) | |
| *F04B 13/02* | (2006.01) | |
| *F04F 5/10* | (2006.01) | |
| *G01L 19/00* | (2006.01) | |
| *G01L 19/16* | (2006.01) | |
| *G01F 23/16* | (2006.01) | |
| *G01N 35/10* | (2006.01) | |
| *G08B 5/36* | (2006.01) | |

(52) U.S. Cl.
CPC ............ *G08B 21/182* (2013.01); *F04B 13/02* (2013.01); *F04F 5/10* (2013.01); *G01F 23/162* (2013.01);
(Continued)

(58) Field of Classification Search
CPC ................ G08B 21/182; G01L 19/003; G01L 19/08–19/12; G01L 19/16; G01N 35/1016; G01N 2035/1025
See application file for complete search history.

(56) References Cited

U.S. PATENT DOCUMENTS

| | | | |
|---|---|---|---|
| 4,756,329 A | 7/1988 | Cloup | |
| 5,094,102 A * | 3/1992 | Fryer | .................... G01F 23/161 340/618 |

(Continued)

FOREIGN PATENT DOCUMENTS

| | | |
|---|---|---|
| EP | 0 255 791 B1 | 12/1989 |
| EP | 0 885 357 B1 | 8/2002 |

(Continued)

OTHER PUBLICATIONS

International Search Report, dated Aug. 11, 2015, from corresponding PCT Application.

*Primary Examiner* — Laura Nguyen
(74) *Attorney, Agent, or Firm* — Young & Thompson

(57) ABSTRACT

A device (1) for monitoring the operation of a dosage dispenser (2) which includes a suction pipe (5) suitable for being plunged into the liquid additive (3) contained in a container (6), the monitoring device including elements for detecting the suction of liquid additive and elements for displaying operating parameters of the dosage dispenser; the detection elements include a tube (10), separate from the suction pipe (5), one end (10b) of which is configured to be plunged into the container of liquid additive, and the other end (10c) is kept stationary relative to the suction pipe in
(Continued)

order to be located outside the container, the other end (10c) being closed and provided with a sensor of the air pressure inside the tube, the sensor outputting an electrical signal, and elements for using the signal from the sensor, connected to the outlet of the sensor, to provide information on the operation.

10 Claims, 3 Drawing Sheets

(52) U.S. Cl.
CPC ............ *G01L 19/003* (2013.01); *G01L 19/16* (2013.01); *G01N 35/1016* (2013.01); *G08B 5/36* (2013.01)

(56) References Cited

U.S. PATENT DOCUMENTS

| | | | |
|---|---|---|---|
| 6,129,526 A | 10/2000 | Kelly | |
| 8,747,075 B1 * | 6/2014 | Gandini | A01K 63/047 |
| | | | 119/247 |
| 2013/0145841 A1 * | 6/2013 | Smaidris | G01F 23/14 |
| | | | 73/302 |
| 2013/0202456 A1 | 8/2013 | Lucas et al. | |

FOREIGN PATENT DOCUMENTS

| | | | | |
|---|---|---|---|---|
| FR | 2 798 705 A1 | 3/2001 | | |
| GB | 2 157 368 A | 10/1985 | | |
| JP | 2012-87631 A | 5/2012 | | |
| WO | 2012/046162 A1 | 4/2012 | | |
| WO | WO 2012046162 A1 * | 4/2012 | ............. | F04B 9/105 |

* cited by examiner

DEVICE FOR MONITORING THE OPERATION OF A DOSAGE DISPENSER OF A LIQUID ADDITIVE IN A MAIN LIQUID, AND DOSAGE DISPENSER PROVIDED WITH SUCH A DEVICE

The invention relates to a device for monitoring the operation of a dosage dispenser of a liquid additive in a main liquid which actuates the dosage dispenser according to suction and delivery stages, which dosage dispenser includes a suction pipe suitable for plunging into the liquid additive contained in a container, the monitoring device including means for detecting the suction of liquid additive and means for displaying operating parameters of the dosage dispenser which are suitable for transmitting, using data provided by the detecting means, a piece of information at least when the level of liquid additive in the container reaches a lower limit, and when an untimely increase in the level occurs in the container.

FR 2 798 705 proposes a monitoring device of this type including, as means for detecting the suction of liquid additive, two pressure sensors placed at the ends of a pressure loss element arranged in the suction pipe.

Such a pressure loss element slows the additive suction flow rate for a determined driving pressure difference. Moreover, this pressure loss element increases the risks of blocking the suction pipe. Furthermore, the installation of pressure sensors at the terminals of this element complicates the manufacture of the monitoring device.

The main aim of the invention is to provide a device for monitoring the operation of a liquid additive dosage dispenser which no longer, or to a lesser extent, has the disadvantages set out above, while remaining a simple and reliable embodiment and implementation.

According to the invention, the device for monitoring the operation of a dosage dispenser of a liquid additive in a main liquid, of the type defined above, is characterized in that the means for detecting the suction of liquid additive comprise:
a tube, separate from the suction pipe, one end of which is provided for plunging into the container of liquid additive, and the other end of which is held fixed relative to the suction pipe in order to be located outside the container, this other end being closed and provided with a sensor for the air pressure in the tube, which sensor outputs an electrical signal,
and means for utilizing the signal from the sensor, which means are connected to the output of the sensor, in order to provide the operational information.

The suction pipe of the dosage dispenser is free of any element creating a pressure loss and the installation of the pressure sensor at the upper end of the tube is relatively simple.

Advantageously, the monitoring device includes a detector device for the pressure of the liquid in a suction pipe segment, mounted in the wall of the pipe while leaving the passage section of the pipe free, the detector device being arranged downstream of a suction valve and allowing the number of pressure peaks and pumping cycles to be counted, and the utilization means include calculating means for determining the pumped additive volume from the number of pressure peaks detected and means for comparison between the additive value estimated from the means of utilizing the signal from the air pressure sensor, and that determined from the pressure peaks detected.

The utilization means can include a microprocessor programmed to process the various information coming from the air pressure sensor and from the detector device for pressure of the liquid in the suction pipe.

The display means can include light-emitting diodes of different colors, and/or a display screen. The operating information can be provided in alphanumerical form, and/or in light form using light-emitting diodes of different colors, and/or in the form of a sound signal.

The monitoring device can include a housing with a suction pipe segment and devices for connection to a lower pipe and to an upper pipe segment located in a sleeve of the dosage dispenser. Advantageously, the tube is removably fixed in the housing.

The tube can be parallel to the suction pipe, or oblique relative to this pipe.

The invention also relates to a dosage dispenser of a liquid additive in a main liquid which actuates the dosage dispenser according to suction and delivery stages, which dosage dispenser includes a suction pipe suitable for plunging into the liquid additive contained in a container, and an operation monitoring device including means for detecting the suction of liquid additive, and means for displaying operating parameters of the dosage dispenser which are suitable for transmitting a piece of information at least when the level of liquid additive in the container reaches a lower limit, and when an untimely increase in the level in the container occurs, characterized in that the means for detecting the suction of liquid additive comprise:
a tube, separate from the suction pipe, the lower end of which is provided for plunging into the container of liquid additive, and the upper end of which is held fixed relative to the suction pipe, in order to be located outside the container, this upper end being closed and provided with a sensor for the air pressure in the tube, which sensor outputs an electrical signal,
and means for utilizing the signal from the sensor, which means are connected to the output of the sensor.

The upper end of the tube can be closed, at least in part, by the air pressure sensor. In an alternative, the air pressure sensor can be arranged in the wall of the tube, proximate the upper end.

Advantageously, the dosage dispenser includes a detector device for the pressure variation of the liquid in a segment of the suction pipe, which is sensitive to the pressure in this pipe, and mounted in the wall of the pipe while leaving the passage section of the pipe free, the detector device being arranged downstream of a suction valve and allowing the number of pressure peaks and pumping cycles to be counted.

The invention consists, apart from the arrangements disclosed above, in a certain number of other arrangements described more explicitly hereafter using exemplary embodiments described with reference to the appended drawings, but which are in no way limiting, wherein.

Figure 2:
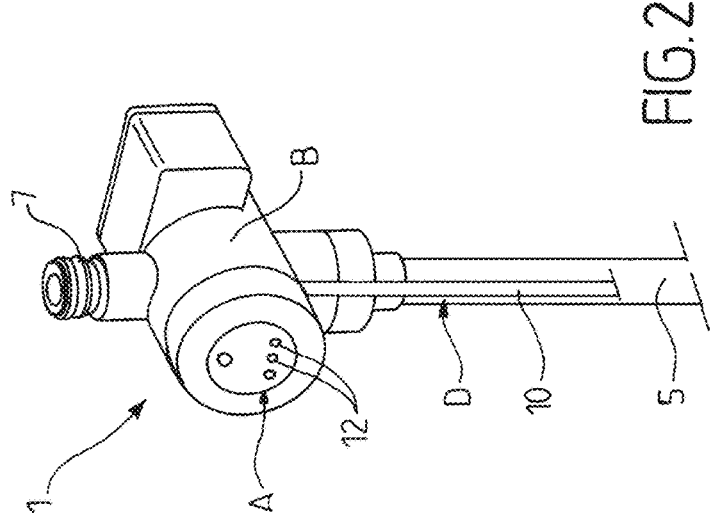
FIG. 2 is an outer perspective view on a larger scale of the monitoring device of FIG. 1, the tube only being partially shown.

Referring to FIG. 1-4 of the drawings, it is possible to see a first embodiment of a device 1 for monitoring the operation of a dosage dispenser 2 of a liquid additive 3 in a stream of main liquid which flows in a conduit 4 connected to the dosage dispenser 2. The driving source of the dosage dispenser is formed by the stream of main liquid which actuates the dosage dispenser, which operates without driving electricity. Such dosage dispensers are known, particularly from the patent EP 0 255 791 B1, and from EP 0 885 357 B1 and WO 2012/046 162.

The dosage dispenser 2 includes a suction pipe 5 suitable for plunging into a volume of liquid additive contained in a container 6. The pipe 5 is connected to a suction pipe segment 5b (FIG. 4) provided in the monitoring device 1. The housing B of the device 1 includes, opposite the tube 5, a connecting piece 7 suitable for being connected to the lower part of a cylindrical sleeve 8 of the dosage dispenser 2. Another segment, which is not visible, of the suction pipe is provided in the sleeve 8, and receives a piston which moves back and forth to provide the suction and delivery stages. A suction valve 9 (FIG. 4) is advantageously arranged in a bottom part of the segment 5b of the suction pipe. The valve 9 opens during the suction and closes again during the delivery of the liquid additive extracted dose in the stream of main liquid.

Suction detecting means D comprise a tube 10 which is separate from the suction pipe 5, the lower end 10b of which is provided for plunging into the container 6 of liquid additive. The other upper end 10c of the tube is closed and provided with a sensor 11 for the air pressure in the tube 10.

The upper end 10c is fixed in the housing B of the device 1, in particular by tight-fitting in a hole of this housing, preferably according to an assembly allowing the removal and replacement of the tube 10.

The sensor 11 outputs an electrical signal. Means E for utilizing the signal are connected to the output of the sensor. The utilization means E advantageously comprise a microprocessor programmed to provide, using data coming from the sensor 11, a piece of operating information which appears on display means A comprising, according to the exemplary embodiment of FIG. 2, several light-emitting diodes 12 of different colors, particularly green, yellow and red, to indicate, according to the diode that is lit, that the operation is correct (lit green diode) or is moderately satisfactory (lit yellow diode) or is defective (lit red diode).

In particular, a piece of warning information, with a lit red diode, is provided when the level of liquid additive in the container 6 reaches a lower limit corresponding to the practically empty container, or when an untimely increase in the level of liquid in the container 6 occurs. Such an increase in the level can result, in particular, from a leak of main liquid to the container 6.

Advantageously, on the segment 5b of the suction pipe, in the housing B of the device 1, a detector device 13 for the pressure of the liquid is mounted in the wall of the segment, while leaving the passage section free. The detector device 13 is installed downstream of the suction valve 9, above this valve according to FIG. 4. The term "downstream" is to be understood according to the direction of flow of the liquid additive when it is sucked. The detector device 13 is connected to the utilization means E and allows the counting of the pressure peaks and of the pumping cycles corresponding to delivery stages of the dosage dispenser, for which the valve 9 is closed.

WO 2012/046 162 provides a detector device of this type.

The utilization means E comprise, in particular, a microprocessor and are advantageously programmed as calculating means to determine the pumped additive volume from the number of dosage dispenser cycles detected by the device 13.

Preferably, the utilization means E comprise means for comparison between the pumped additive volume determined from the information provided by the detector device 13, and the pumped additive volume deduced from the variation in pressure in the tube 10, provided by the sensor 11.

More precisely, the variation in pressure measured by the sensor 11 corresponds to the variation in height of the additive in the container 6, which allows the volume of liquid sucked to be deduced for a container of known section. This volume is compared to that obtained by multiplying the number of pressure peaks, in the segment 5b, by the volumetric displacement of a suction of additive liquid. By multiplying the number of pressure peaks by the volumetric displacement of the dosage dispenser for the main liquid, the utilization means E determine the total volume of liquid passing through the dosage dispenser in a given time. By obtaining the ratio of the pumped additive volume to said total volume, the utilization means E allow the dose of additive in the main liquid to be determined.

Figure 5:
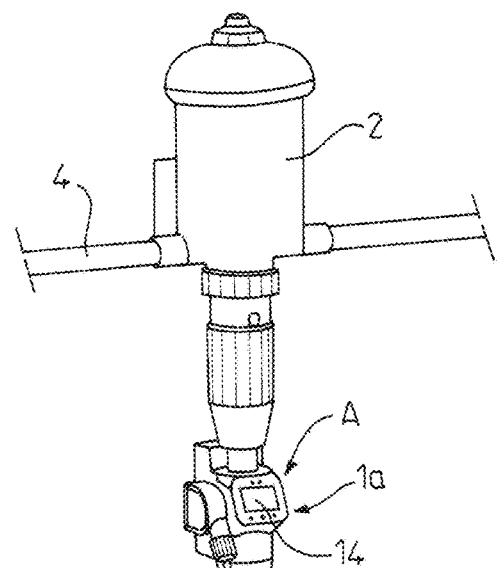
FIG. 5 shows, in an outer perspective and front view, a dosage dispenser provided with an alternative embodiment of the monitoring device.
Figure 5:
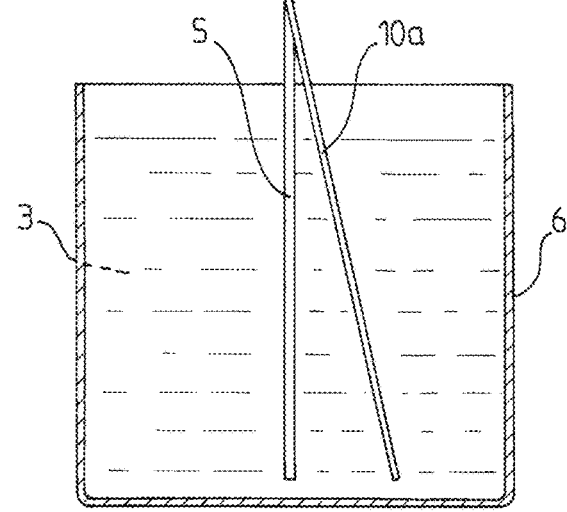
Figure 7:
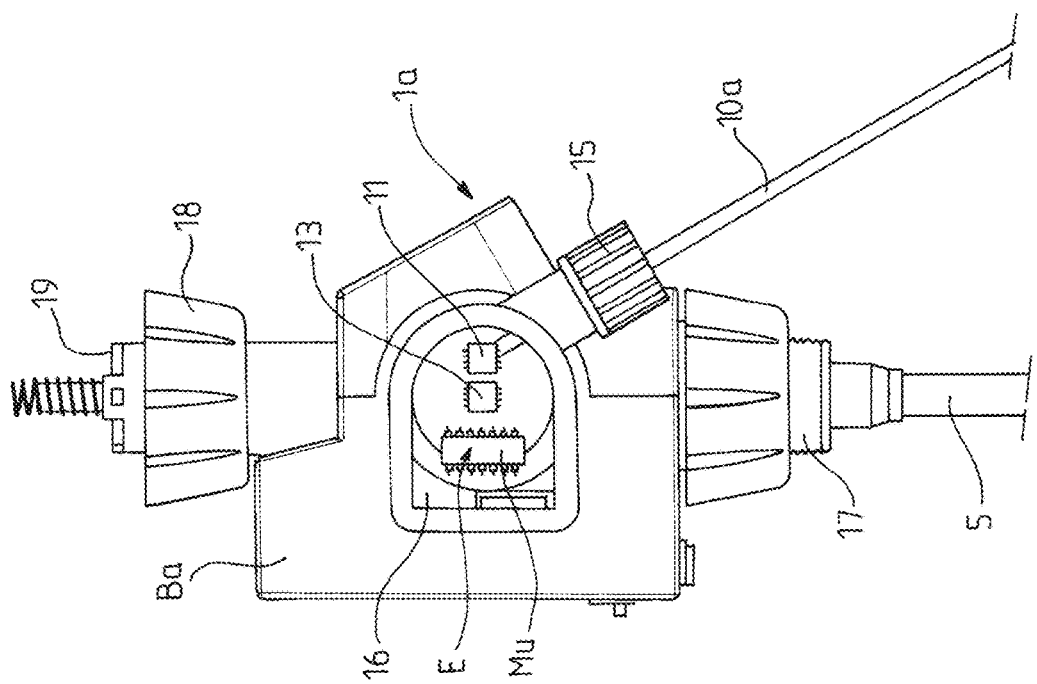
FIG. 7 is a left-hand view with respect to FIG. 6.
Figure 6:
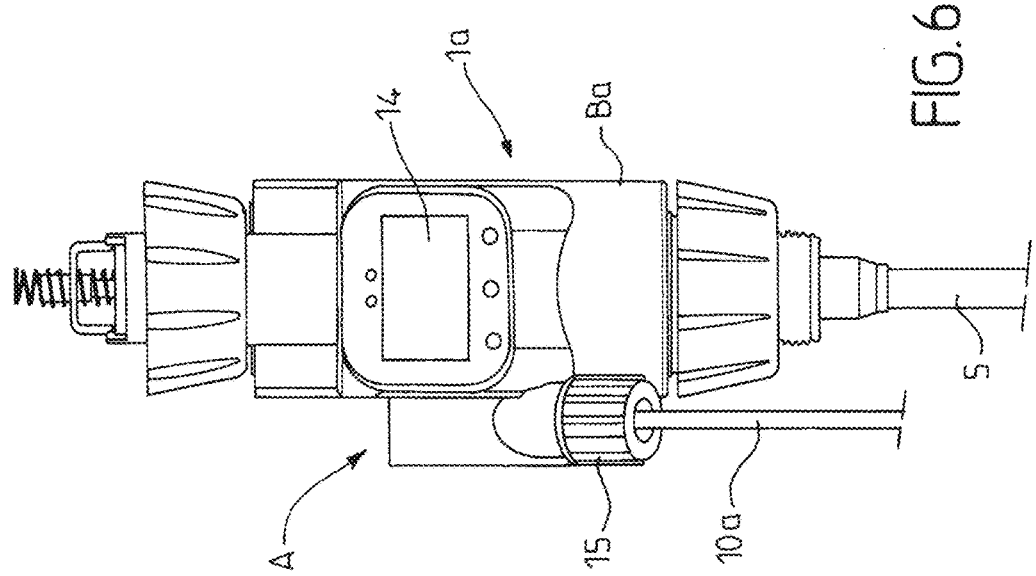
FIG. 6 is a front view on a larger scale of the monitoring device of FIG. 5.

Referring to FIGS. 5-7, it is possible to see an alternative embodiment 1a of the monitoring device according to the invention. The elements that are identical or similar to elements already described in relation to the previous figures are designated by the same numerical references possibly followed by the letter "a", without the description thereof being repeated in detail.

Figure 1:
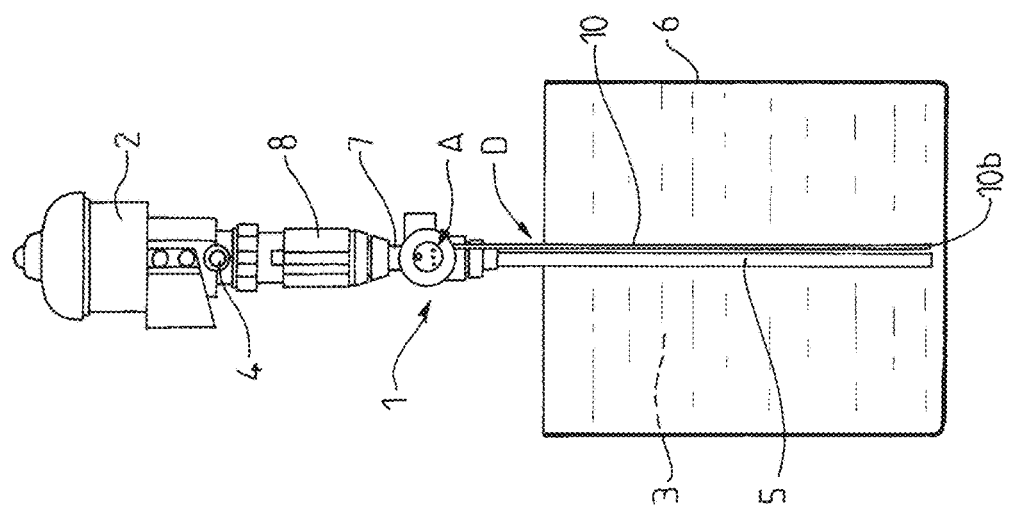
FIG. 1 is a front view of a liquid additive dosage dispenser provided with a monitoring device according to the invention.
Figure 3:
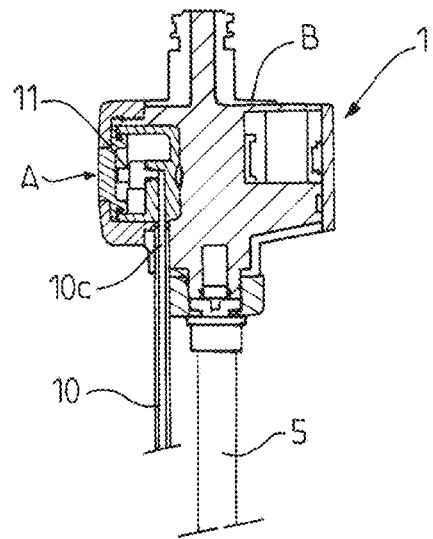
FIG. 3 is a section of the device of FIG. 2 through a mid-perpendicular vertical plane of the display device, and passing through the geometric axis of the tube.
Figure 4:
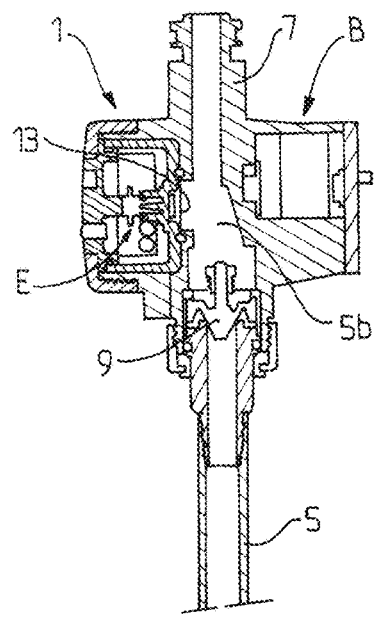
FIG. 4 is a section of the device of FIG. 2 through a vertical plane, which is offset with respect to the plane of FIG. 3, passing through the geometric axis of the suction pipe, and orthogonal to the display screen.

The tube 10a, which is separate from the suction pipe 5, instead of being vertical and parallel to the pipe 5 as in the case of FIG. 1, is somewhat inclined, particularly by approximately 20°, in relation to the vertical. The display means A are made up of a, preferably liquid crystal, screen 14, on which the utilization means E allow alphanumerical messages to be displayed.

The tube 10a is held, in the upper part thereof, by a clamping device 15 having a nut and clamping chuck (not visible) about the tube 10a. The upper end of the tube opens into a cavity 16 (FIG. 7) of the housing Ba where a microprocessor Mu which is part of the utilization means E is arranged. The microprocessor Mu is connected to the pressure sensor 11 and to the screen 14. In normal operation, the cavity 16 is closed by a lid. The power supply of the electronic components of the monitoring device is provided by an electric cell or battery accommodated in the housing Ba, or B in the case of FIG. 1-4.

The detector device for pressure 13 in the suction pipe is also arranged in the cavity 16 and connected to the microprocessor Mu.

The bottom part of the housing Ba includes a connection 17 for linking to the pipe 5. Provided in the continuation of the connector 17 is, at the upper part on the housing Ba, a connection device 18 for linking with the lower end of the sleeve 8 of the dosage dispenser. A valve 19 is provided at the upper end of the connection 18.

Irrespective of the embodiment, the device for monitoring the operation of the dosage dispenser according to the invention allows, using the air pressure measured in the tube 10, 10a, for detection of fault situations such as:

a delivery of the additive and possibly of the main liquid 4, into the container 6, during and outside of the operation of the dosage dispenser, by detecting a liquid level greater than a determined limit;

a level of liquid, in the container 6, less than a determined base limit;

under-dosing.

The combination of the air pressure sensor 11 and of the detector 13, for pressure of the liquid in the suction pipe, and the processing by the utilization means E of the information obtained allows the flow rate to be precisely estimated and a reliable dosage estimation to be conducted. The operational incidents are quickly signaled.

With a container 6 of calibrated section, tracking the level of liquid in this container, thanks to the pressure sensor 11, allows a genuine suction flowmeter to be provided.

The invention claimed is:

1. A device for monitoring an operation of a dosage dispenser of a liquid additive in a main liquid which actuates the dosage dispenser according to suction and delivery stages, wherein the dosage dispenser includes a suction pipe (5) suitable for plunging into the liquid additive contained in a container, the monitoring device including means (D) for detecting the suction of liquid additive and means (A) for displaying operating parameters of the dosage dispenser which are suitable for transmitting, using data provided by the detecting means, a piece of information at least when the level of liquid additive in the container reaches a lower limit, and when an untimely increase in the level occurs in the container, wherein the means for detecting the suction of liquid additive comprises:

a tube (10, 10a), separate from the suction pipe (5), one end (10b) of which is provided for plunging into the container (6) of liquid additive, and the other end (10c) of which is held fixed relative to the suction pipe in order to be located outside the container, this other end (10c) being closed and provided with a sensor (11) for an air pressure in the tube (10, 10a), wherein the sensor outputs an electrical signal, and utilization means (E) for utilizing the signal from the sensor (11), wherein the utilization means is connected to the output of the sensor, in order to provide the operating parameters, the device further including a detector device (13) for a pressure of the liquid additive in a suction pipe segment, mounted in the wall of the pipe while leaving the passage section of the pipe free, the detector device being arranged downstream of a suction valve (9) and allowing a number of pressure peaks and a number of pumping cycles to be counted, and the utilization means (E) including calculating means for determining a pumped additive volume from the number pressure peaks detected and means for comparison between an additive value estimated from the utilization means (E) for utilizing the signal from the sensor (11), and an additive value determined from the number pressure peaks detected.

2. The device as claimed in claim 1, wherein the utilization means (E) includes a microprocessor (Mu) programmed to process various information coming from the air pressure sensor (11) and from the detector device (13) for the pressure of the liquid additive in the suction pipe.

3. The device as claimed in claim 1, wherein the display means (A) includes light-emitting diodes (12) of different colors.

4. The device as claimed in claim 1, wherein the display means (A) includes a display screen (14) on which the operating parameters are provided in alphanumerical form.

5. The device as claimed in claim 1, further including a housing (B, Ba) with a suction pipe segment (5b) and devices for connection to a lower pipe (5) and to an upper pipe segment located in a sleeve (8) of the dosage dispenser (2).

6. The device as claimed in claim 5, wherein the tube (10, 10a) is removably fixed in the housing (B, Ba).

7. The device as claimed in claim 1, wherein the tube (10) is parallel to the suction pipe (5).

8. The device as claimed in claim 1, wherein the tube (10a) is oblique relative to the suction pipe (5).

9. A dosage dispenser of a liquid additive in a main liquid which actuates the dosage dispenser according to suction and delivery stages, which dosage dispenser includes a suction pipe (5) suitable for plunging into the liquid additive contained in a container, and an operation monitoring device (1, 1a) including means (D) for detecting the suction of liquid additive, and means (A) for displaying operating parameters of the dosage dispenser which are suitable for transmitting a piece of information at least when the level of liquid additive in the container reaches a lower limit, and when an untimely increase in the level in the container occurs, wherein the means (D) for detecting the suction of liquid additive comprises:

a tube (10, 10a), separate from the suction pipe (5), the lower end (10b) of which is provided for plunging into the container of liquid additive, and the upper end (10c) of which is held fixed relative to the suction pipe, in order to be located outside the container, this upper end being closed and provided with a sensor (11) for an air pressure in the tube, wherein the sensor outputs an electrical signal, and means (E) for utilizing the signal from the sensor, wherein the means (E) for utilizing is connected to the output of the sensor the dosage dispenser further including a detector device (13) for a pressure variation of the liquid additive in a segment (5b) of the suction pipe, which is sensitive to the pressure variation of the liquid additive in this pipe, and mounted in the wall of the pipe while leaving the passage section of the pipe free, the detector device (13) being arranged downstream of a suction valve (9) and allowing a number of pressure peaks and a number of pumping cycles to be counted, and the means (E) for utilizing including calculating means for determining a pumped additive volume from the number of pressure peaks detected and means for comparison between an additive value estimated from the means (E) for utilizing the signal from the air pressure sensor (11), and an additive value determined from the number of pressure peaks detected.

10. The dosage dispenser as claimed in claim 9, wherein the upper end (10c) of the tube is closed, at least in part, by the air pressure sensor (11).

* * * * *